United States Patent
Welz et al.

(10) Patent No.: US 8,110,010 B2
(45) Date of Patent: Feb. 7, 2012

(54) COATED COLORING AGENTS

(75) Inventors: Carolin Welz, Hamburg (DE); Hartmut Manneck, Klein Wesenberg (DE); Astrid Kleen, Hamburg (DE); Mustafa Akram, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/163,821

(22) Filed: Jun. 20, 2011

(65) Prior Publication Data

US 2011/0247149 A1    Oct. 13, 2011

Related U.S. Application Data

(63) Continuation of application No. PCT/EP2009/066838, filed on Dec. 10, 2009.

(30) Foreign Application Priority Data

Dec. 19, 2008  (DE) .................. 10 2008 063 800

(51) Int. Cl.
*A61Q 5/10*      (2006.01)
(52) U.S. Cl. ............. 8/405; 8/406; 8/435; 8/526; 8/552; 8/594
(58) Field of Classification Search ............... 8/405, 406, 8/435, 526, 552, 594
See application file for complete search history.

(56) References Cited

U.S. PATENT DOCUMENTS

| 5,053,051 | A | 10/1991 | Tennigkeit et al. | |
| 7,458,992 | B2 * | 12/2008 | Schmenger et al. | 8/405 |

FOREIGN PATENT DOCUMENTS

| EP | 1726289 A2 | 11/2006 |
| EP | 1752191 A1 | 2/2007 |
| EP | 1820487 A1 | 8/2007 |
| EP | 1905418 A2 | 4/2008 |
| WO | 2009013779 A2 | 1/2009 |

OTHER PUBLICATIONS

Schrader, Karlheinz. Grundlagen and Rezepturen der Kosmetika (Fundamentals and Formulations of Cosmetics), 2, Hüthig Buch Verlag GmbH, Heidelberg 1989.

* cited by examiner

*Primary Examiner* — Eisa Elhilo
(74) *Attorney, Agent, or Firm* — David P. LeCroy

(57) ABSTRACT

Agents for coloring keratin-containing fibers, in particular human hair, that contain encased oxidation dye precursor products. More-uniform coloring, which is independent of which strands are wetted first or last with the coloring product, is thereby ensured. The casing of the oxidation dye precursor products is made up of an encapsulating material made of methacrylic-acid, methacrylic acid-ester, or vinyl-acetate homo- or copolymers, or shellac, as well as at least one release agent. Contact time is equalized over time and shortened overall, resulting in a reduction in hair damage due to excessively long contact times. A method for manufacturing coloring agents for keratinic fibers, containing coated particles is also provided.

14 Claims, No Drawings

COATED COLORING AGENTS

CROSS REFERENCE TO RELATED APPLICATIONS

The present application is a continuation of International Application No. PCT/EP2009/066838 filed 10 Dec. 2009, which claims priority to German Patent Application No. 10 2008 063 800.5 filed 19 Dec. 2008, both of which are incorporated herein by reference.

The present invention relates to agents for coloring keratin-containing fibers, particularly human hair, containing encased oxidation dye precursor products. More uniform coloring is thereby ensured, regardless of which strands are wetted first or last with the coloring product. The casing of the oxidation dye precursor products is made up of an encapsulating material of methacrylic-acid, methacrylic acid-ester, vinyl-acetate homo- or copolymers, or shellac, as well as at least one release agent. The overall result is that contact time is equalized over time and shortened overall, yielding a reduction in hair damage due to excessively long contact times. A further subject of the present invention relates to a method for manufacturing coloring agents for keratinic fibers containing coated particles.

Modification of the shape and color of hair represents an important sector of modern cosmetology. The appearance of the hair can thereby be adapted both to current fashion trends and to the individual desires of the particular person. Consumers turn to color-modifying agents in order to impart fashionable colors to hairstyles, or to conceal graying or white hair using fashionable or natural color shades. These agents are intended to produce not only the desired coloring performance but also the least possible damage to the hair, and should preferably possess additional care-providing properties.

The skilled artisan is familiar with a variety of color systems depending on coloring requirements for making available color-modifying cosmetic agents, in particular for the skin or for keratin-containing fibers such as human hair.

Oxidation coloring agents are used for permanent, intense color results with corresponding fastness properties. Such coloring agents usually contain oxidation dye precursor products, developer components and coupler components. Under the influence of oxidizing agents or atmospheric oxygen, the developer components form, among one another or by coupling to one or more coupler components, the actual dyes. Oxidation coloring agents are notable for outstanding, long-lasting coloring results. For natural-looking colors, however, it is usually necessary to use a mixture of a larger number of oxidation dye precursor products. In many cases, substantive dyes are also utilized for tinting.

It is usual to use as developer components primary aromatic amines having a free or substituted hydroxy or amino group located in the para- or ortho-position, heterocyclic hydrazones, diaminopyrazole derivatives, and 2,4,5,6-tetraaminopyrimidine and derivatives thereof. Coupler components that are typically used are m-phenylenediamine derivatives, naphthols, pyridine derivatives, resorcinol and resorcinol derivatives, pyrazolones, and m-aminophenols.

For temporary coloring, it common to use coloring or toning agents containing substantive dyes as a coloring component. These are dye molecules that absorb directly onto the substrate and do not require an oxidizing process in order to form the color. Included among these dyes are, for example, henna, which has been known since antiquity for coloring the body and hair. These color results are, as a result, much more sensitive to shampooing than are the oxidation-based colors, so that a (very often undesirable) shift in tint, or even a visible homogeneous loss of color occurs much more quickly.

Despite their advantageous color properties, oxidizing hair coloring agents have disadvantages for the user.

Firstly, use of the oxidizing agents for coloring or to develop the actual color results in damage to the hair structure and hair surface. The hair becomes brittle, its elasticity decreases, and combability declines. Secondly, oxidizing coloring agents usually require an alkaline pH to produce coloring, particularly from pH 9.0 to 11.5. These pH values are necessary in order to ensure opening of the outer cuticle and allow penetration of the active species (dye precursor products and/or hydrogen peroxide) into the hair. The alkaline environment, however, represents another source of damage to the hair and its structure, which again becomes increasingly significant with a longer application time. Expansion of the outer cuticle furthermore causes the hair to have an unpleasant surface feel, also resulting in degraded combability when both wet and dry. This creates for the consumer an increased need to use additional post-treatment agents such as conditioners.

A further problem faces the consumer in achieving uniform color results. For uniform coloring, it is particularly important to control the starting point of coloring processes. This problem is especially severe when many selected hair areas, distributed over the head, need to be colored. Coloring agents are often used only to lighten individual hair strands in order to produce a visually interesting hair color. In the conventional "highlighting" process, individual hair strands are placed into pieces of foil, treated with the coloring preparation, and wrapped in the foil. Because the application process is protracted, contact times on the successively treated strands are different, resulting in color that, because they are varied, is undesirable, with strands of different colors. Greater time independence when applying and rinsing out the coloring agents is therefore desirable for the user, especially the professional user.

There has therefore been no lack of attempts to develop suitable methods for delaying the onset of coloring.

One approach is represented by selective encapsulation of ingredients. Documents EP 1 820 487 A1 and WO 2005/044208 A1 disclose coated dye-containing pellets. EP 1 726 289 A2 discloses encapsulated reducing agents in coloring agents. The encasing of pH adjusting agents in hair coloring agents is known from EP 1 752 191 A2, which discloses encased alkalizing agents, and from WO 89/065531 A1, which describes encapsulated acidifying agents.

The present invention is based on making available agents for coloring keratin fibers that enable a uniform and homogeneous coloring result, particularly with the "highlighting" technique. The intention was to avoid the over-coloring of individual strands that are acted upon by the application mixture earlier in the process that other strands.

It has now been found that the aforesaid objects can be achieved by making available coloring agents containing at least one particulate constituent having a particle core made up of oxidation dye precursor products and a coating made up of specific encasing substances and release agents.

Because the oxidation dye precursor products are coated, the onset of the actual coloring process is delayed and a greater time independence for the user when applying the coloring agent is thus achieved. Even in cases of poor time management on the part of the user in terms of rinsing out the strands, a uniform and therefore low-impact color result is obtained.

The present invention is therefore firstly directed towards an agent for coloring keratinic fibers, particularly human hair, containing at least one particulate constituent having a particle core containing at least one oxidation dye precursor product, and a casing surrounding the core, wherein the casing is made up of at least one encapsulation material chosen from
- a) homo- and/or copolymers of methacrylic acid and/or of methacrylic acid esters (methacrylates), and/or
- b) homo- and/or copolymers of vinyl acetate, and/or
- c) shellac and at least one release agent.

"Keratinic fibers" or "keratin fibers" refer to furs, wool, feathers, and in particular human hair. Although agents according to the present invention are suitable chiefly for coloring keratin fibers, there is in principle no obstacle to using them in other areas as well.

Agents according to the present invention can be made available in a large number of presentation forms, for example, in the form of pastes, powders, tablets, etc., provided they contain at least one particulate ingredient that is surrounded by a casing. In terms of utilization convenience, however, the agents are preferably present as coloring powders. Agents according to the present invention that are present as a particle mixture (i.e., "in powder form") are preferred embodiments of the present invention.

Agents according to the present invention contain at least one particulate core having at least one oxidation dye precursor product. The agents therefore contain, as a first ingredient, at least one oxidation dye precursor product.

Oxidation dye precursor products can be divided in terms of their reaction behavior into two categories: developer components and coupler components.

Developer components can form, with themselves, the actual dye. They can therefore be present in the agent as the only color-modifying compounds. In a preferred embodiment, the agents contain at least one oxidation dye precursor product of the developer type and/or coupler type. Coloring agents according to the present invention preferably contain at least one oxidation dye precursor product of the developer type, and at least one oxidation dye precursor product of the coupler type.

The developer and coupler components are usually used in free form. For substances having amino groups, however, it may be preferred to use them in salt form, particularly in the form of hydrochlorides and hydrobromides or sulfates.

Preferred p-phenylenediamines as oxidation dye precursor products of the developer type include 1,4-diaminobenzene (p-phenylenediamine), 1,4-diamino-2-methylbenzene (p-toluylenediamine), 1,4-diamino-2-chlorobenzene (2-chloro-p-phenylenediamine), 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxan, as well as physiologically acceptable salts thereof. p-Phenylenediamine derivatives that are particularly preferred according to the present invention are selected from at least one compound of the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine, as well as physiologically acceptable salts thereof.

It may furthermore be preferred according to the present invention to use as developer components compounds having at least two aromatic nuclei that are substituted with amino and/or hydroxyl groups. Preferred binuclear developer components include: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, as well as physiologically acceptable salts thereof. Particularly preferred binuclear developer components are selected from among N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, or one of the physiologically acceptable salts thereof.

It may furthermore be preferred according to the present invention to use as a developer component a p-aminophenol derivative or one of the physiologically acceptable salts thereof. Preferred p-aminophenols include 4-aminophenol, N-methyl-4-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof. Particularly preferred compounds are 4-aminophenol, 4-amino-3-methylphenol, 4-amino-2-aminomethylphenol, 4-amino-2-(1,2-dihydroxyethyl)phenol, and 4-amino-2-(diethylaminomethyl)phenol.

Developer components can also be chosen from o-aminophenol and derivatives thereof such as 2-amino-4-methylphenol, 2-amino-5-methylphenol, or 2-amino-4-chlorophenol.

Developer components can furthermore be chosen from heterocyclic developer components, for example, from pyrimidine derivatives, pyrazole derivatives, pyrazolopyrimidine derivatives, and physiologically acceptable salts thereof. Preferred pyrimidine derivates are 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Preferred pyrazole derivatives are the compounds that are selected from among 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically acceptable salts thereof, in particular 4,5-diamino-1-(2-hydroxyethyl)pyrazole. Among the pyrazolo[1,5-a]pyrimidines, the following may be mentioned in particular: pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]-pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine, as well as physiologically acceptable salts thereof and tautomeric forms thereof, if a tautomeric equilibrium exists.

Preferred developer components include p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)-propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N-bis-(2-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as physiologically acceptable salts thereof. Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole, as well as physiologically acceptable salts thereof.

Developer components are preferably used in an amount of from 0.005 to 20 wt %, preferably 0.1 to 5 wt %, based on the ready-to-use oxidation dye.

Coupler components alone do not produce any significant color in oxidizing coloring, but instead always require the presence of developer components. It is therefore preferred according to the present invention that when at least one coupler component is used, at least one developer component is additionally utilized.

Preferred 3-aminophenol coupler components include 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and physiologically acceptable salts thereof. Preferred 3-diaminobenzene coupler components include 3-aminoaniline (m-phenylenediamine), 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2'-hydroxyethyl)aminobenzene, and physiologically acceptable salts thereof. Preferred 1,2-diaminobenzene coupler components include 3,4-diaminobenzoic acid and 2,3-diamino-1-methylbenzene, and the physiologically acceptable salts of all the aforementioned compounds. Preferred di- or trihydroxybenzenes and derivatives thereof include resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives include 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and physiologically acceptable salts thereof. Preferred napthalene derivatives having at least one hydroxy group include 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred indole derivatives include 4-hydroxyindole, 6-hydroxyindole, 7-hydroxyindole, and physiologically acceptable salts thereof Preferred indoline derivatives include 4-hydroxyindoline, 6-hydroxyindoline, and 7-hydroxyindoline, and physiologically acceptable salts thereof. Preferred pyrimidine derivatives include 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and physiologically acceptable salts thereof.

Coupler components particularly preferred according to the present invention include 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or of physiologically acceptable salts thereof. Resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine, and 1-naphthol, as well as one of the physiologically acceptable salts thereof, are very particularly preferred.

Coupler components are preferably used in an amount of from 0.005 to 20 wt %, preferably 0.1 to 5 wt %, based on the ready-to-use oxidation dye.

The following combinations of oxidation dye precursor products of the developer type and of the coupler type are particularly preferred in the context of the present invention. Further dye precursor products can, however, also be combined with the oxidation dye precursor products recited as a combination: p-toluylenediamine/resorcinol; p-toluylenediamine/2-methylresorcinol; p-toluylenediamine/5-amino-2-methylphenol; p-toluylenediamine/3-aminophenol; p-toluylenediamine/2-(2,4-diaminophenoxy)ethanol; p-toluylenediamine/1,3-bis(2,4-diaminophenoxy)propane; p-toluylenediamine 1-methoxy-2-amino-4-(2-hydroxyethylamino)benzene; p-toluylenediamine/2-amino-3-hydroxypyridine; p-toluylenediamine/1-naphthol; 2-(2-hydroxyethyl)-p-phenylenediamine/resorcinol; 2-(2-hydroxyethyl)-p-phenylenediamine/2-methylresorcinol; 2-(2-hydroxyethyl)-p-phenylenediamine/5-amino-2-methylphenol; 2-(2-hydroxyethyl)-p-phenylenediamine/3-aminophenol; 2-(2-hydroxyethyl)-p-phenylenediamine/2-(2,4-diaminophenoxy)ethanol; 2-(2-hydroxyethyl)-p-phenylenediamine/1,3-bis-(2,4-diaminophenoxy)propane; 2-(2-hydroxyethyl)-p-phenylenediamine/1-methoxy-2-amino-4-(2-hydroxyethylamino)benzene; 2-(2-hydroxyethyl)-p-phenylenediamine/2-amino-3-hydroxypyridine; 2-(2-hydroxyethyl)-p-phenylenediamine/1-naphthol; 2-methoxymethyl-p-phenylenediamine/resorcinol; 2-methoxymethyl-p-phenylenediamine/2-methylresorcinol; 2-methoxymethyl-p-phenylenediamine/5-amino-2-methylphenol; 2-methoxymethyl-p-phenylenediamine/3-aminophenol; 2-methoxymethyl-p-phenylenediamine/2-(2,4-diaminophenoxy)ethanol; 2-methoxymethyl-p-phenylenediamine/1,3-bis-(2,4-diaminophenoxy)propane; 2-methoxymethyl-p-phenylenediamine/1-methoxy-2-amino-4-(2-hydroxyethylamino)benzene; 2-methoxymethyl-p-phenylenediamine/2-amino-3-hydroxypyridine; 2-methoxymethyl-p-phenylenediamine/1-naphthol; N-(4-amino-3-methylphenyl)-N-[3-(1H-imidazol-1-yl)propyl]amine/resorcinol; N-(4-amino-3-methylphenyl)-N-[3-(1H-imidazol-1-yl)propyl]amine/2-methylresorcinol; N-(4-amino-3-methylphenyl)-N-[3-(1H-imidazol-1-yl)propyl]amine/5-amino-2-methylphenol; N-(4-amino-3-methylphenyl)-N-[3-(1H-imidazol-1-yl)propyl]amine/3-aminophenol; N-(4-amino-3-methylphenyl)-N-[3-(1H-imidazol-1-yl)propyl]amine/2-(2,4-diaminophenoxy)ethanol; N-(4-amino-3-methylphenyl)-N-[3-(1H-imidazol-1-yl)propyl]amine/1,3-bis(2,4-diaminophenoxy)propane; N-(4-amino-3-methylphenyl)-N-[3-(1H-imidazol-1-yl)propyl]amine/1-methoxy-2-amino-4-(2-hydroxyethylamino)benzene; N-(4-amino-3-methylphenyl)-N-[3-(1 H-imidazol-1-yl)propyl]amine/2-amino-3-hydroxypyridine; N-(4-amino-3-methylphenyl)-N-[3-(1H-imidazol-1-yl)propyl]amine/1-naphthol; 4,5-diamino-1-(2-hydroxyethyl)pyrazole/resorcinol; 4,5-diamino-1-(2-hydroxyethyl)pyrazole/2-methyl resorcinol; 4,5-diamino-1-(2-hydroxyethyl)pyrazole/5-amino-2-methylphenol; 4,5-diamino-1-(2-hydroxyethyl)pyrazole/3-aminophenol; 4,5-diamino-1-(2-hydroxyethyl)pyrazole/2-(2,4-diaminophenoxy)ethanol; 4,5-diamino-1-(2-hydroxyethyl)pyrazole/1,3-bis(2,4-diaminophenoxy)propane; 4,5-diamino-1-(2-hydroxyethyl)pyrazole/1-methoxy-2-amino-4-(2-hydroxyethylamino)benzene; 4,5-diamino-1-(2-hydroxyethyl)pyrazole/2-amino-3-hydroxypyridine; 4,5-diamino-1-(2-hydroxyethyl)pyrazole/1-naphthol.

In order to achieve balanced and subtle shading, it is advantageous according to the present invention if further color-imparting components are present in the agent.

In a further embodiment, agents according to the present invention can additionally contain at least one substantive dye. These are dyes that are absorbed directly onto the hair and do not require an oxidizing process in order to form the color. Substantive dyes are usually nitrophenylenediamines, nitraminophenols, azo dyes, anthraquinones, or indophenols.

It may be inventively preferred if the particle core contains, in addition to the oxidation dye precursor products, further components such as diluents and/or carriers.

As a further feature of the present invention, the particle core containing oxidation dye precursor products is surrounded by a casing made up of at least one encapsulation material chosen from a) homo- and/or copolymers of methacrylic acid and/or of methacrylic acid esters (methacrylates), and/or b) homo- and/or copolymers of vinyl acetate, and/or c) shellac and at least one release agent.

In preferred agents according to the invention, the casing is at least 50 wt %, more preferably at least 70 wt %, and particularly at least 80 wt % of a) homo- and/or copolymers of methacrylic acid and/or of methacrylic acid esters, and/or b) homo- and/or copolymers of vinyl acetate, and/or c) shellac.

Encapsulation agents particularly suitable according to the present invention are homo- and/or copolymers of methacrylic acid and/or of methacrylic acid esters. Among these, copolymers of methacrylic acid and/or of methacrylic acid esters are preferred. Particularly preferred representatives are described below.

A particularly suitable casing material comprises copolymers of methacrylic acid, methyl acrylate, and methyl meth acrylate. These contain monomer units having the following structures:

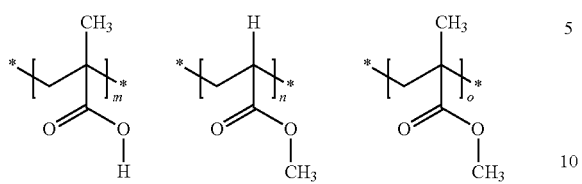

wherein the indices m, n, and o vary depending on the molecular weight of the polymer and do not indicate that these are block copolymers. Structural units can instead be present in statistically distributed fashion in the molecule.

In preferred agents, the casing contains at least one copolymer of methacrylic acid, methyl acrylate, and methyl methacrylate.

In particularly preferred polymers of this type, the molar ratio of methacrylic acid to the two esters is greater than 1, preferably greater than 5. Particularly preferred agents according to the present invention have a molar ratio of ester groups to free carboxy groups in the copolymer of 1:5 to 1:12. Even further preferred polymers of this type have molecular weights of about 220 kDa. Particularly preferred agents are those wherein the copolymer of methacrylic acid, methyl acrylate, and methyl methacrylate has a molecular weight from 200 to 250 kDa.

A further particularly suitable casing material is copolymers of methacrylic acid and ethyl acrylate. These contain monomer units having the following structures:

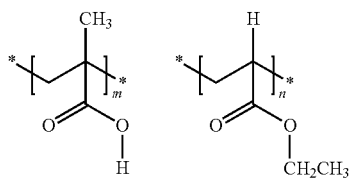

wherein m and n vary depending on the molecular weight of the polymer and do not indicate that these are block copolymers. Structural units can instead be present in statistically distributed fashion in the molecule.

In preferred agents, the casing contains at least one copolymer of methacrylic acid and ethyl acrylate. In particularly preferred polymers of this type, the molar ratio of methacrylic acid to the ester is approximately 1. Particularly preferred agents have molar ratio of ester groups to free carboxy groups in the copolymer of 1:0.9 to 0.9:1.

Even more preferred polymers of this type have molecular weights of about 250 kDa. Particularly preferred agents according to the present invention are those wherein the copolymer of methacrylic acid and ethyl acrylate has a molecular weight from 225 to 275 kDa.

A further particularly suitable casing material is copolymers containing methacrylic acid esters having cationic groups, particularly made up of (ω-trialkylammonioalkyl) methacrylates. Agents wherein the casing contains at least one copolymer of (2-trimethylammonioethyl) methacrylate chloride are particularly preferred. This contains monomer units of formula (I)

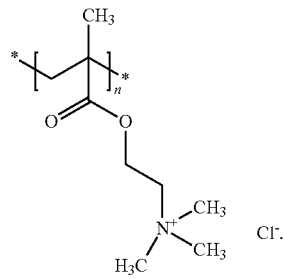

Esters of methacrylic acid and/or esters of acrylic acid have proven particularly successful as (an) additional monomer(s) in the copolymers having monomer units of formula (I).

In preferred agents, the casing of the particles therefore contains copolymers of (2-trimethylammonioethyl) methacrylate chloride and at least one additional monomer chosen from ethyl methacrylate, methyl methacrylate, ethyl acrylate, and methyl acrylate.

Agents according to the present invention in which the copolymer having monomer units of formula (I) contains ethyl methacrylate as (an) additional monomer(s) are preferred.

Agents according to the present invention in which the copolymer having monomer units of formula (I) contains methyl methacrylate as (an) additional monomer(s) are further preferred.

In addition to or instead of the further methacrylic acid esters, acrylic acid esters can also be polymerized into the copolymer having monomer units of formula (I). Agents according to the present invention in which the copolymer having monomer units of formula (I) contains ethyl acrylate as (an) additional monomer(s) are preferred here.

Agents according to the present invention in which the copolymer having monomer units of formula (I) contains methyl acrylate as (an) additional monomer(s) are further preferred.

A further particularly suitable casing material is copolymers of methyl methacrylate and ethyl acrylate. These contain monomer units having the following structures:

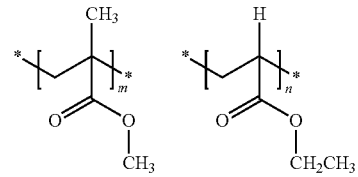

wherein m and n vary depending on the molecular weight of the polymer and do not indicate that these are block copolymers. Structural units can instead be present in statistically distributed fashion in the molecule.

In preferred agents according to the present invention, the casing contains at least one copolymer of methyl methacrylate and ethyl acrylate.

In particularly preferred polymers of this type, the molar ratio of methacrylic acid to the ester is approximately 1. Particularly preferred agents have a molar ratio of ester groups to free carboxy groups in the copolymer of 1:0.9 to 0.9:1.

Even further preferred polymers of this type have molecular weights of about 800 kDa. Particularly preferred agents are those wherein the copolymer of methyl methacrylate and ethyl acrylate has a molecular weight from 750 to 850 kDa.

Preferred acrylic acid/methacrylic acid/methacrylic acid ester copolymer grades are marketed by the BASF company under the trade names Eudragit FS 30D, Eudragit L30D-55 (=Kollicoat MAE 30DP), Eudragit RS 30D, Eudragit RL 30D, and Eudragit NE 30D.

Encapsulation agents particularly suitable according to the present invention include homo- and/or copolymers of vinyl acetate. Among the copolymers of vinyl acetate, copolymers thereof with ethylene (ethylene-vinyl acetate copolymers, abbreviated EVA or EVAC) and/or with vinyl chloride (abbreviated VCEVAC [often also, incorrectly, VCEVA]) or VCVAC [also PVCA]) are of particular significance and can be used according to the present invention.

Agents according to the present invention having the homopolymer as a coating material for the particles, in which context the casing contains polyvinyl acetate, are particularly preferred.

Polyvinyl acetate (abbreviated PVAC) is obtained by radical polymerization of acetic acid vinyl ester (vinyl acetate). Linkage of the monomers upon construction of the polymer chain occurs very largely (up to 98%) as head/tail polymerization, and only to a small extent as head/head polymerization. Macromolecules of polyvinyl acetates therefore contain groupings of mostly type I (head/tail), and only a few of type II (head/head), as characteristic basic units:

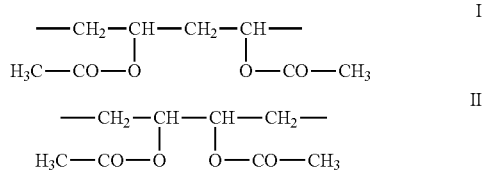

Polyvinyl acetates can be manufactured using substance polymerization, solution polymerization, suspension (bead) polymerization, or emulsion polymerization methods. Preferred polyvinyl acetates have molecular weights from 10,000 to 1,500,000 g/mol, and a molecular weight-dependent glass transition temperature of approximately 28° C. They are amorphous, odorless, and tasteless products having a high resistance to light and weathering, insoluble in water and soluble in many organic solvents (esters, ethers, ketones, halogenated hydrocarbons, among others). A particularly suitable polyvinyl acetate is marketed by the BASF company under the trade name Kollicoat SR30D.

A further encapsulating agent that is particularly suitable according to the present invention is shellac. Shellac is obtainable from the secretion of lac insects (*Kerria lacca* or *Laccifer lacca*), and occurs as a stiff resin having an average molecular weight of approx. 1000 g/mol. It is made up predominantly of partly unsaturated hydroxycarboxylic acids that are present either as esters with one another or as a lactone. The principal components are aleuritic acid (aleuric acid, 9,10,16-trihydroxypalmitic acid) with up to approx. 32 wt % shellolic acid.

Shellac is readily soluble in alcohols, organic acids, and aqueous bases, less so in esters and ketones, and insoluble in hydrocarbons and water.

The recovery of shellac involves collecting the secretion deposited onto branches, removing twig residues, and decoloring with alkali. From this "seed lac," the actual shellac is isolated as a wax-containing or wax-free resin.

The shellac (commercial names: Lemon, TN, Ivory, Orange, Honey), as produced after a melt filtration process in which melted seed lac is filtered in order to remove accompanying substances, still contains a natural wax proportion of approx. 4 to 6 wt %.

Bleached shellac occurs as a white powder when chlorine bleach liquor (sodium hypochlorite) acts on seed lac. It is available both as wax-containing and wax-free.

Wax-free shellac, which is obtained from seed lac by solvent extraction accompanied by (partial) decolorizing using activated carbon and is present after drying in the form of thin flakes, is marketed as "flake shellac." This wax-free shellac is marketed, for example, under the trade names Shellac SSB 55 Astra FL (wax content max. 0.2 wt %), Shellac CZSH 2 (wax content max. 0.25 wt %), Mantrolac R 49 (wax content max. 0.2 wt %), and Angelo Dewaxed Garnet Shellac.

Wax-free or low-wax shellac is preferably used according to the present invention as an encapsulation material. "Low-wax" shellac here is shellac having a weight proportion of wax of at most 0.5 wt %.

Because of its large number of functional groups, shellac is easy to harden and modify chemically. In particular, it can be easily mixed with further polymeric encapsulation agents.

Encapsulation agents are mutually miscible, and can be combined with one another to achieve a specific time delay.

The casing surrounding the particle core further contains, in addition to the encapsulation material, at least one release agent. The release agent serves to prevent sticking or caking of the encased particles during the manufacturing process and/or during storage and/or, if applicable, during mixing with further preparations.

Preferred release agents according to the present invention include partial glycerides of fatty acids, metal soaps, and inorganic powdered release agents chosen from graphic, talc, and mica.

Partial glycerides of fatty acids that are suitable release agents include mono- and di-fatty acid glyceryl esters. Examples of such partial glycerides are glycerol monostearate, glycerol distearate, glycerol monooleate, glycerol dioleate, glycerol monodecanoate, glycerol didecanoate, glycerol monolaurate, glycerol dilaurate, glycerol monomyristate, glycerol dimyristate, glycerol monopalmitate, or glycerol dipalmitate. Partial glycerides of fatty acids that are suitable are also derived from naturally or synthetically occurring fatty acid mixtures. Examples thereof are, in particular, glycerol monococoate, glycerol dicocoate, glycerol monocetearate, glycerol dicetearate, glycerol monotallow ester, and glycerol ditallow ester. A particularly preferred release agent is glycerol monostearate.

Metal soaps that are suitable release agents are, in particular, soaps of polyvalent cations, in particular of calcium, lead, magnesium, aluminum, and zinc cations. Suitable fatty acids are, in particular, lauric acid, myristic acid, palmitic acid, oleic acid, and stearic acid. Soaps that derive from stearic acid are particularly preferred. Metal soaps particularly preferred according to the present invention are magnesium stearate, calcium stearate, and zinc stearate. Magnesium stearate is particularly preferred.

Further release agents according to the present invention are inorganic powdered release agents selected from graphite, talc, and mica. A preferred inorganic powdered release agent is talc (magnesium silicate).

Particularly preferred agents are those wherein the casing contains talc as a release agent.

In preferred agents, the casing is at most 50 wt %, more preferably at most 30 wt %, and in particular 20 wt % of one or more release agents.

If the casing is not made up exclusively of encapsulating agents and release agents, it can contain further ingredients such as dyes and scents or adjuvants.

Particularly preferred agents according to the present invention contain plasticizers in the casing for better casing elasticity. Plasticizers derive preferably from the dialkyl phthalate group, in particular diethyl phthalate, triethyl citrate, glycerol triacetate, and/or the polyethylene glycols.

In a further embodiment, agents according to the present invention contain coated particles whose casing surrounding the particle core additionally contains at least one disintegration agent.

Disintegration agents are often also described in the literature as disintegrating agents or bursting agents. Substances of this kind are incorporated into the polymer casing in order to shorten its disintegration time. This disintegration, or bursting, occurs in particular because of an increase in volume due to water penetration (swelling).

Such disintegration agents or disintegration accelerators are understood as adjuvants that ensure the rapid breakdown of shaped elements in water.

Cellulose-based disintegration agents are preferred disintegration agents in the context of the present invention. Suitable celluloses are made up of approx. 500 to 5000 glucose units, and consequently have average molar weights from 50,000 to 500,000. Also usable in the context of the present invention as cellulose-based disintegration agents are cellulose derivatives obtainable from cellulose via polymer-analogous reactions. Such chemically modified celluloses include, for example, products of esterification or etherification processes in which hydroxy hydrogen atoms have been substituted. Celluloses in which the hydroxy groups have been replaced with functional groups that are not bound via an oxygen atom can also, however, be used as cellulose derivatives. Cellulose derivatives includes, for example, alkali celluloses, carboxymethyl cellulose (CMC), cellulose esters and ethers, and aminocelluloses. Cellulose derivatives are preferably not used as the only cellulose-based disintegration agent, but in a mixture with cellulose. The cellulose-derivative concentration of these mixtures is preferably below 50 wt %, more preferably below 20 wt %, based on the cellulose-based disintegration agent. Pure cellulose that is free of cellulose derivatives is particularly preferred for use as a cellulose-based disintegration agent. Suitable carboxymethyl cellulose derivatives are marketed, for example, under the trade names Tylopur by the Clariant company, or Ac-Di-Sol by the FMC company.

Microcrystalline cellulose can be used as a further cellulose-based disintegration agent or as a constituent of that component. This microcrystalline cellulose is obtained by partial hydrolysis of celluloses under conditions wherein only the amorphous regions (approx. 30% of the total cellulose mass) of the celluloses are attacked and dissolve completely, but the crystalline regions (approx. 70%) remain undamaged. A subsequent disaggregation of the microfine celluloses resulting from hydrolysis yields the microcrystalline celluloses having primary particle sizes of approx. 5 µm and are compactable, for example, into granules having an average particle size of 200 µm. Suitable microcrystalline cellulose is commercially obtainable, for example, under the trade name Emcocel from the JRS company, or Avicel from the FMC company.

Starch can also be used preferably as a disintegration agent in the context of the present invention. Starch usable according to the present invention is usually obtained from vegetable raw materials, such as rice, soybeans, potatoes, or corn. Starch can unmodified or (by analogy with cellulose) modified starch. Particularly preferred starch modifications are furnished by esterification and etherification reactions, particularly ethers obtained from reactions with hydroxycarboxylic acids. A starch modification that is particularly suitable according to the present invention is the mixture of sodium carboxymethyl starch and sodium glycol starch that is marketed by the JRS Pharma company under the trade name Explotab.

Disintegration agents based on corn starch are particularly preferred according to the present invention. Suitable modified corn starches are obtainable, for example, under the trade names Glycolys from the Roquette company, or Starch 1000 from the Colorcon company.

Lastly, disintegration agents made up of crosslinked, water-insoluble polyvinylpyrrolidinone (PVP) represent a further class of disintegration agents particularly suitable according to the present invention. The advantageous crosslinking of this PVP modification is based principally on entanglements and loops of the individual polymer strands with one another. A PVP-based disintegration agent that is particularly preferred according to the present invention is marketed by the BASF company under the trade name Kollidon CL.

Casings according to the present invention that surround the particle core contain the disintegrating adjuvant in quantities from 0.05 to 20 wt %, preferably 0.1 to 10 wt %, based on total weight of the dried casing.

In a further embodiment, agents according to the invention contain coated particles whose casing surrounding the particle core additionally contains at least one pore-forming agent.

Pore-forming agents are additionally incorporated into the coating and cause pores to form in the surface of the coating. This increases the diffusion rate for hydrophilic substances, particularly water, into the polymer casing.

Suitable pore-forming agents according to the present invention are polyvinylpyrrolidinone, sugars and sugar alcohols such as lactose, sucrose, sorbitol, and mannitol, polyethylene glycols having fewer than 600 ethylene oxide units, as well as cellulose derivatives such as hydroxypropyl cellulose, hydroxypropylmethyl cellulose, methyl cellulose, and mixtures thereof. Preferred pore-forming agents are polyvinylpyrrolidinones (PVP), which are marketed, for example, under the trade name Kollidon by the BASF company.

According to the present invention, the weight proportion of the pore-forming agent in the dried casing is from 0.05 to 20 wt %, particularly from 0.1 to 10 wt %, based on total weight of the casing.

In a process according to the present invention for manufacturing the casing, the encapsulation agent and release agent, as well as the applicable adjuvants, are homogeneously mixed and sprayed as an aqueous dispersion, by fluidized bed technology (using the bottom spray method with or without the Wurster process, or the tangential spray method), onto the powder particles made up at least of oxidation dye precursor products, and at the same time are dried in the air flow so that a uniform, almost 100% layer surrounds the powder particles.

As an alternative to fluidized bed technology, coatings with the aforesaid film materials are alternatively possible using spouted bed technology. A further possibility for encasing powder particles is represented by melt extrusion technology.

It may be advantageous to encapsulate the particle cores with a multi-layer casing. Dispersions that are identical or that differ in terms of their composition regarding encapsulation materials, release agents and adjuvants, can be applied successively, and optionally can also be applied using different coating techniques.

It has proven to be particularly advantageous if the particulate constituents contain silicon dioxide as an additional release agent for particularly effective elimination of sticking or caking of the particles. In particular, amorphous and/or pyrogenic silicon dioxide, marketed, for example, under the trade names Syloid 244FP by Grace GmbH, or Aerosil by the Evonik company, can be used as an additional release agent. For this purpose, the particulate constituents can be mixed directly with silicon dioxide, in particular as long as the particles have not yet completely dried.

Particularly preferably according to the present invention, the particulate constituents containing silicon dioxide as an additional release agent are manufactured by spraying the particulate constituents, already coated with one or more casings, with an aqueous dispersion containing silicon dioxide, and are then dried. A silicon dioxide-containing dispersion of this kind preferably contains from 5 to 30 wt % silicon dioxide and is marketed, for example, by Evonik under the trade name Aerodisp W.

In a further embodiment, subsets of the particle cores are encapsulated with different encasing or coating materials. In a further manufacturing process step, these partial batches are mixed with one another at specific proportions.

Agents according to the present invention contain coated particles having an average particle diameter from 50 to 500 μm, preferably 100 μm to 250 μm.

In further preferred agents, the coating material is applied in a specific quantity onto the particles to be coated. Agents according to the present invention wherein the casing accounts for 10 to 70 wt % of the weight of the coated particles are preferred here.

In the case of oxidizing color processes, development of the color can be effected using atmospheric oxygen. It is preferred, however, to utilize a chemical oxidizing agent, particularly when a lightening effect on human hair is desired in addition to the color result. This lightening effect can be desired regardless of the coloring method. Suitable oxidizing agents are persulfates, peroxodisulfates, chlorites, hypochlorites, and in particular hydrogen peroxide and/or a solid deposition product thereof onto organic or inorganic compounds.

In order to prevent a premature, undesired reaction of the oxidation dye precursor products as a result of the oxidizing agent, the oxidation dye precursor products and the oxidizing agent itself are usefully packaged separately from one another and brought into contact only immediately before use.

In a further embodiment of the present invention, preferred agent are produced immediately before use by mixing at least two preparations, the at least two preparations being made available in at least two separately packaged containers, with one container (I) containing a coloring preparation (A), and a further container (II) containing an oxidizing agent preparation (B) containing at least one oxidizing agent. Coloring preparation (A) contains at least one particulate constituent having a particle core containing at least one oxidation dye precursor product and comprises a casing surrounding the core, wherein the casing is made up of at least one encapsulation material chosen from
    a) homo- and/or copolymers of methacrylic acid and/or of methacrylic acid esters (methacrylates), and/or
    b) homo- and/or copolymers of vinyl acetate, and/or
    c) shellac,
and at least one release agent.

Agents of this embodiment are marketed preferably as multi-component packaging units (kit of parts).

In a preferred embodiment, the coloring preparation (A) is present in the form of a powder or fine granules. In this embodiment, the container (I) is made available preferably in the form of a small bag, a sachet, a pouch, or also in the form of a can, optionally reclosable.

When the coloring preparation (A) is present in the form of a powder or as fine granules, it may be advantageous for manufacture of the ready-to-use coloring agent to first mix the coloring preparation (A) with an additional liquid cream or emulsion base (C), and then add an oxidizing agent preparation (B).

In a further embodiment of the present invention, preferred agents are produced immediately before use by mixing at least three preparations, the at least three preparations being made available in at least three separately packaged containers, with one container (I) containing a coloring preparation (A), one container (Ia) an emulsion preparation (C), and a further container (II) containing an oxidizing agent preparation (B) containing at least one oxidizing agent. Coloring preparation (A) contains at least one particulate constituent having a particle core containing at least one oxidation dye precursor product and comprises a casing surrounding the core, wherein the casing is made up of at least one encapsulation material chosen from
    a) homo- and/or copolymers of methacrylic acid and/or of methacrylic acid esters (methacrylates), and/or
    b) homo- and/or copolymers of vinyl acetate, and/or
    c) shellac,
and at least one release agent, and preparations (A) and (C) are first intimately mixed, and preparation (B) is then added.

Oxidizing agent preparation (B) preferably contains, as an oxidizing agent, hydrogen peroxide and/or a solid product of deposition thereof onto organic or inorganic compounds, such as urea, melamine, and sodium borate.

The amount of oxidizing agent in the ready-to-use agent is preferably 0.5 to 12 wt %, more preferably 2 to 10 wt %, and particularly preferably 3 to 6 wt % (calculated as 100% $H_2O_2$), based on the ready-to-use agent.

Oxidizing agent preparations of this kind are preferably aqueous, flowable oxidizing agent preparations. Preferred preparations are those wherein the flowable oxidizing agent preparation contains, based on its weight, 40 to 95 wt %, preferably 50 to 90 wt %, particularly preferably 55 to 85 wt %, more preferably 60 to 80 wt %, and in particular 65 to 75 wt % water.

According to the invention, the oxidation dye can also be applied onto the hair together with a catalyst that activates oxidation of the dye precursor products (e.g., by atmospheric oxygen). Such catalysts are, for example, certain enzymes, iodides, quinones, or metal ions.

It is advantageous if the oxidizing agent preparations contain at least one stabilizer or complexing agent. Particularly preferred stabilizers are phenacetin, alkali benzoates (sodium benzoate) and salicylic acid.

Use of complexing agents is also preferred. Complexing agents are substances that can complex metal ions. Preferred complexing agents are chelate complexing agents, that is, substances that form cyclic compounds with metal ions, a single ligand occupying more than one coordination site on a central atom, i.e. being at least "double-toothed." The number of bound ligands depends on the coordination number of the central ion.

Preferred complexing agents include nitrogen-containing polycarboxylic acids, in particular EDTA, and phosphonates, by preference hydroxyalkane- or aminoalkanephosphonates and in particular 1-hydroxyethane-1,1-diphosphonate (HEDP) or the di- or tetrasodium salt thereof, and/or ethylenediaminetetramethylenephosphonate (EDTMP) or the hexasodium salt thereof, and/or diethylenetriaminepentamethylenephosphonate (DTPMP) or the hepta- or octasodium salt thereof.

The coloring preparation, and optionally the oxidizing agent preparation, contain further adjuvants and additives. For example, it has proven to be preferred according to the present invention if the coloring preparation and/or the oxidizing agent preparation contain at least one thickening agent. No limitations exist in principle with regard to this thickening agent. Both organic and entirely inorganic thickening agents can be utilized.

To further enhance the performance of the oxidizing agent preparation, at least one optionally hydrated $SiO_2$ compound can additionally be added to the composition according to the present invention. It may be preferred to use optionally hydrated $SiO_2$ compounds in quantities from 0.05 wt % to 15 wt %, preferably 0.15 wt % to 10 wt %, and very preferably 0.2 wt % to 5 wt %, based on the anhydrous composition according to the present invention. The quantitative indications reflect the concentration of $SiO_2$ compounds (without their water component) in the agents.

In principle, the present invention is subject to no limitations in terms of the optionally hydrated $SiO_2$ compounds. Silicic acids, oligomers and polymers thereof, and salts thereof, are preferred. Preferred salts are alkali salts, in particular potassium and sodium salts. Sodium salts are very particularly preferred. Very particularly preferred according to the present invention are water glasses that are constituted by a silicate of the formula $(SiO_2)_n(Na_2O)_m(K_2O)_p$, where n is a positive rational number and m and p, mutually independently, are a positive rational number or 0, provided that at least one of the parameters m or p is different from 0, and that the ratio between n and the sum of m and p is from 1:4 to 4:1. In addition to the components described by the empirical formula, the water glasses can also contain further additives such as phosphates or magnesium salts in small quantities.

Water glasses that are particularly preferred according to the present invention are marketed, inter alia, by the Henkel company under the designations Ferrosil 119, Natronwasserglas 40/42, Portil A, Portil AW, and Portil W, and by the Akzo company under the designation Britesil C20.

Preparation (C), and/or optionally oxidizing agent preparation (B), are preferably packaged as flowable preparations.

An emulsifier or surfactant is preferably added to the flowable preparations (B) and/or (C). Depending on the application sector, surface-active substances can be designated as either surfactants or emulsifiers, and are chosen from anionic, cationic, zwitterionic, amphoteric, and nonionic surfactants and emulsifiers.

All anionic surface-active substances suitable for use on the human body are suitable as anionic surfactants in preparations according to the present invention. These have an anionic group imparting water solubility, for example, a carboxylate, sulfate, sulfonate, or phosphate group, and a lipophilic alkyl group having approximately 8 to 30 carbon atoms. Glycol or polyglycol ether groups, ester, ether, and amide groups, as well as hydroxyl groups, can additionally be contained in the molecule. Preferred anionic surfactants are alkyl sulfates, alkyl ether sulfates, and ethercarboxylic acids having 10 to 18 carbon atoms in the alkyl group and up to 12 glycol ether groups in the molecule.

"Zwitterionic surfactants" refers to those surface-active compounds having in the molecule at least one quaternary ammonium group and at least one carboxylate, sulfonate, or sulfate group. Particularly suitable zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Amphoteric surfactants" are those surface-active compounds having in the molecule, in addition to a $C_8$ to $C_{24}$ alkyl or acyl group, at least one free amino group and at least one —COOH or —$SO_3H$ group, and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Particularly preferred amphoteric surfactants are N-cocalkylaminopropionate, cocacylaminoethylaminopropionate, and $C_{12-18}$ acyl sarcosine.

It has further proven to be advantageous if coloring agents according to the invention contain further, nonionogenic surface-active substances. Nonionic surfactants contain as a hydrophilic group, for example, a polyol group, a polalkylene glycol ether group, or a combination of polyol and polyglycol ether groups. $C_8$ to $C_{22}$ alkyl mono- and oligoglycosides, and ethoxylated analogs thereof, are particularly suitable as nonionic surfactants. The non-ethoxylated compounds, in particular, have proven to be particularly suitable. Alkylene oxide addition products with saturated linear fatty alcohols and fatty acids, having respectively 2 to 30 mol ethylene oxide per mol fatty alcohol or fatty acid, have proven to be preferred further nonionic surfactants. Preparations having outstanding properties are likewise obtained if they contain fatty acid esters of ethoxylated glycerol as nonionic surfactants.

Anionic, nonionic, zwitterionic, or amphoteric surfactants are used in quantities from 0.1 to 45 wt %, preferably 1 to 30 wt %, and very particularly preferably from 1 to 15 wt %, based on total quantity of the ready-to-use agent.

Cationic surfactants of the quaternary ammonium compound, esterquat, and amidoamine types are likewise preferred according to the present invention. Preferred quaternary ammonium compounds are ammonium halides, in particular chlorides and bromides, such as alkyltrimethylammonium chlorides, dialkyldimethylammonium chlorides, and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known by the INCI names Quaternium-27 and Quaternium-83. The long alkyl chains of the aforementioned surfactants preferably comprise 10 to 18 carbon atoms. The quaternized protein hydrolysates represent further cationic surfactants usable according to the present invention.

Alkylamidoamines are usually manufactured by amidation of natural or synthetic fatty acids and fatty acid cuts with dialkylaminoamines. One compound from this group of substances that is particularly suitable according to the present invention is the stearamidopropyldimethylamine available commercially under the designation Tegoamid® S 18.

Esterquats are known substances that contain both at least one ester function and at least one quaternary ammonium group as a structural element. Preferred esterquats are quaternized ester salts of fatty acids with triethanolamine, quaternized ester salts of fatty acids with diethanol alkylamines, and quaternized ester salts of fatty acids with 1,2-dihydroxypropyldialkylamines. Such products are marketed, for example, under the trademarks Stepantex, Dehyquart and Armocare. The products Armocare VGH-70—an N,N-bis(2-palmitoyloxyethyl)dimethylammonium chloride—and Dehyquart F-75, Dehyquart C-4046, Dehyquart L80, and Dehyquart AU-35, are examples of such esterquats.

Cationic surfactants are present in agents according to the present invention preferably in quantities from 0.05 to 10 wt %, based on the entire agent. Quantities from 0.1 to 5 wt % are particularly preferred.

In a preferred embodiment, nonionic, zwitterionic, and/or amphoteric surfactants, as well as mixtures thereof, can be preferred.

A preferred embodiment of the present invention is one wherein the ready-to-use agent has a pH from 7 to 12, in particular from 8 to 11.5, more preferably from 8.5 to 11.5. The values for purposes of the present invention are pH values that have been measured at a temperature of 22° C.

The pH is usually adjusted using pH adjusting agents. Acidifying and alkalizing agents familiar to one skilled in the art of cosmetics are commonly used to adjust the pH. The alkalizing agents usable for adjusting the pH are typically selected from inorganic salts, in particular of the alkali and alkaline-earth metals, organic alkalizing agents, in particular amines, basic amino acids and alkanolamines, and ammonia. Acidifying agents preferred according to the present invention are edible acids, for example, citric acid, acetic acid, malic acid, or tartaric acid, as well as dilute mineral acids.

Organic alkalizing agents usable according to the present invention are preferably chosen from alkanolamines made up of primary, secondary, or tertiary amines having a $C_2$ to $C_6$ alkyl base element that carries at least one hydroxyl group. Preferred alkanolamines are monoethanolamine and triethanolamine. It has been found in the context of investigations relevant to the present invention, however, that preferred agents additionally contain an inorganic alkalizing agent. The inorganic alkalizing agent is preferably chosen from sodium hydroxide, potassium hydroxide, calcium hydroxide, barium hydroxide, sodium phosphate, potassium phosphate, sodium silicate, potassium silicate, sodium carbonate, and potassium carbonate. Sodium hydroxide and/or potassium hydroxide are very particularly preferred. The basic amino acids usable as alkalizing agents according to the present invention are preferably chosen from L-arginine, D-arginine, D/L-arginine, L-lysine, D-lysine, D/L-lysine; particularly preferably, L-arginine, D-arginine, D/L-arginine is used as an alkalizing agent for purposes of the invention. Lastly, a further preferred alkalizing agent is ammonia.

The alkalizing agents are used preferably in a quantity from 0.05 to 10 wt %, in particular from 0.5 to 5 wt %, based on total weight of the ready-to-use agent.

Agents according to the present invention can also contain further active substances, adjuvants, and additives, for example, nonionic polymers (such as vinylpyrrolidinone/vinyl acrylate copolymers, polyvinylpyrrolidinone and vinylpyrrolidinone/vinyl acetate copolymers, polyethylene glycols, and polysiloxanes); cationic polymers (such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidinone copolymers quaternized with diethyl sulfate, vinylpyrrolidinone/imidazolinium methochloride copolymers, and quaternized polyvinyl alcohol); zwitterionic and amphoteric polymers (such as acrylamidopropyltrimethylammonium chloride/acrylate copolymers and octylacrylamide/methyl methacrylate/t-butylaminoethyl methacrylate/2-hydroxypropyl methacrylate copolymers); anionic polymers (such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymer, methylvinyl ether/maleic acid anhydride copolymers, and acrylic acid/ethyl acrylate/N-t-butylacrylamide terpolymers); further thickening agents (such as agar-agar, guar gum, alginates, gum arabic, karaya gum, locust bean flour, linseed gums, dextrans, cellulose derivatives, e.g. methyl cellulose, hydroxyalkyl cellulose, and carboxymethyl cellulose, starch fractions and derivatives such as amylose, amylopectin, and dextrins, clays such as e.g. bentonite, or entirely synthetic hydrocolloids such as, for example, polyvinyl alcohol); structuring agents (such as glucose, maleic acid, and lactic acid); hair-conditioning compounds (such as phospholipids, soy lecithin, egg lecithin, and kephalins, as well as silicone oils); protein hydrolysates (in particular hydrolysates of elastin, collagen, keratin, milk protein, soy protein, and wheat protein, condensation products thereof with fatty acids, and quaternized protein hydrolysates); fiber-structure-improving active substances (in particular mono-, di- and oligosaccharides such as, for example, glucose, galactose, fructose, fruit sugars, and lactose); defoamers (such as silicones, preferably dimethicone); dyes for coloring the agent; anti-dandruff active substances (such as piroctone olamine, zinc omadine, and climbazol); light-protection agents and UV blockers (in particular derivatized benzophenones, cinnamic acid derivatives, and triazines); active substances (such as panthenol, pantothenic acid, pantolactone, allantoin, pyrrolidinonecarboxylic acids, and salts thereof, as well as bisabolol); vitamins, provitamins, and vitamin precursors (in particular those of the groups A, $B_3$, $B_5$, $B_6$, C, E, F, and H); cholesterol; consistency agents (such as sugar esters, polyol esters, or polyolalkyl ethers); fats and waxes (such as beeswax, Montan wax, and paraffins); fatty acid alkanolamides; swelling and penetration substances (such as glycerol, propylene glycol monoethyl ether, carbonates, hydrogencarbonates, guanidines, ureas, and primary, secondary, and tertiary phosphates); opacifiers (such as latex, styrene/PVP and styrene/acrylamide copolymers); luster agents (such as ethylene glycol mono- and distearate as well as PEG-3 distearate); pigments; perfume oils; propellants (such as propane/butane mixtures, $N_2O$, dimethyl ether, $CO_2$, and air), and antioxidants.

One skilled in the art will arrive at a selection of these further substances in accordance with the desired properties of the agents. With regard to further optional components, as well as the quantities of those components used, reference is made expressly to the relevant manuals known to one skilled in the art, such as Kh. Schrader, Grundlagen and Rezepturen der Kosmetika [Cosmetics fundamentals and formulations], 2nd ed., Hüthig Buch Verlag, Heidelberg, 1989.

Agents according to the present invention are suitable for achieving a uniform and homogeneous color result.

A further subject of the present invention is therefore the use of an agent containing at least one particulate constituent having a particle core containing at least one oxidation dye precursor product and comprises a casing surrounding the core, the casing containing at least one encapsulation material chosen from a) homo- and/or copolymers of methacrylic acid and/or of methacrylic acid esters (methacrylates), and/or b) homo- and/or copolymers of vinyl acetate, and/or
c) shellac,
   and at least one release agent,
to improve the uniformity of coloring of keratinic fibers, in particular human hair.

With regard to preferred embodiments of the use according to the present invention, the statements made concerning the agents according to the present invention apply mutatis mutandis in terms of material selection.

A further subject of the present invention is a method for manufacturing agents for coloring keratinic fibers, comprising in a first step, coating at least one particle core, containing at least one oxidation dye precursor product, with a coating agent, forming a casing that is made up of at least one
a) homo- and/or copolymer of methacrylic acid and/or of methacrylic acid esters, and/or
b) homo- and/or copolymers of vinyl acetate, and/or
c) shellac,
and of at least one release agent,
and in a second step, mixing the coated particle(s) with an aqueous oxidizing preparation containing hydrogen peroxide.

In the first step of the method, at least one particulate ingredient is coated with at least one of the aforementioned substances. This step can be carried out without difficulty in a very wide variety of equipment.

As an alternative to the use of a mixer/granulator, a fluidized bed apparatus can also be used to form the solid coating. Methods according to the present invention in which coating of the particles to be coated is carried out in a fluidized bed apparatus are preferred.

Here as well, liquid can simultaneously be applied onto the grains. Coating can be accomplished simultaneously with drying (for example, in a fluidized bed apparatus in which the granules are impinged upon by a solution or dispersion of at least one of the aforementioned substances and are simultaneously dried), but it is also possible and preferred to perform drying after coating, i.e., subsequently thereto in time.

A sealed coating can be generated by applying a solution or dispersion of the aforementioned substance(s) onto the particles to be coated. This solution or dispersion can also contain further film-forming substances.

Alternative coating methods suitable for the manufacture of compositions according to the present invention are spouted bed coating and melt extrusion methods.

It is particularly effective, in order to prevent sticking or caking of the encased particles, if the particles contain silicon dioxide on the surface as an additional release agent. Here, particles which have been coated with one or more encapsulation layers that may optionally differ in thickness and composition, are sprayed with an aqueous dispersion of silicon dioxide, and dried.

A preferred embodiment of the method according to the present invention is therefore characterized in that the coating of the particle cores is carried out in two stages, the particle cores to be coated being, in a fluidized bed apparatus, in a first stage sprayed (if applicable repeatedly) with a solution or dispersion containing at least
   a) one homo- and/or copolymer of methacrylic acid and/or of methacrylic acid esters, and/or
   b) one homo- and/or copolymer of vinyl acetate, and/or
   c) shellac,
and at least one release agent selected from partial glycerides of fatty acids, metal soaps, and inorganic powdered release agents selected from graphite, talc, and mica, and dried, and in a second stage, sprayed with an aqueous dispersion containing at least silicon dioxide, and dried.

We claim:
1. Agent for coloring keratinic fibers comprising:
   at least one particulate component having a particle core containing at least one oxidation dye precursor product and a casing surrounding the core,
   wherein the casing comprises at least one encapsulation material chosen from
   a) homo- and/or copolymers of methacrylic acid and/or of methacrylic acid esters (methacrylates), and/or
   b) homo- and/or copolymers of vinyl acetate,
   and at least one release agent.
2. Agent according to claim 1, wherein the casing comprises at least 50 wt. %, based on weight of the casing, of
   a) homo- and/or copolymers of methacrylic acid and/or of methacrylic acid esters, and/or
   b) homo- and/or copolymers of vinyl acetate.
3. Agent according to claim 1, wherein the casing further comprises polyvinyl acetate.
4. Agent according to claim 1, wherein the casing further comprises at least one copolymer of methacrylic acid, methyl acrylate, and methyl methacrylate.
5. Agent according to claim 1, wherein the casing further comprises at least one copolymer of methacrylic acid and ethyl acrylate.
6. Agent according to claim 1, wherein the casing further comprises at least one copolymer of (2-trimethylammonioethyl) methacrylate chloride and at least one additional monomer chosen from ethyl methacrylate, methyl methacrylate, ethyl acrylate, and methyl acrylate.
7. Agent according to claim 1, wherein the casing further comprises at least one copolymer of methyl methacrylate and ethyl acrylate.
8. Agent according to claim 1, wherein the release agent is chosen from partial glycerides of fatty acids, metal soaps, and inorganic powdered release agents.
9. Agent according to claim 1, wherein the casing further comprises talc as a release agent.
10. Agent according to claim 1, wherein the particulate component further comprises silicon dioxide as an additional release agent.
11. Agent according to claim 10, wherein the particulate component containing silicon dioxide as an additional release agent are manufactured by spraying the encased particulate component with an aqueous dispersion containing silicon dioxide, and then dried.
12. Agent according to claim 1, wherein the casing further comprises at least one pore-forming agent.
13. Method for manufacturing agents for coloring keratinic fibers, comprising:
   in a first step, coating at least one particle core containing at least one oxidation dye precursor product with a coating agent, thereby forming a casing comprising at least one
   a) homo- and/or copolymer of methacrylic acid and/or of methacrylic acid esters, and/or
   b) homo- and/or copolymers of vinyl acetate,
   and at least one release agent, and
   in a second step, mixing the coated particle(s) with an aqueous oxidizing preparation containing hydrogen peroxide.
14. Method according to claim 13, wherein the coating of the particle cores comprises:
   spraying the particle cores in a fluidized bed apparatus with a solution or dispersion comprising at least a) one homo- and/or copolymer of methacrylic acid and/or of methacrylic acid esters, and/or
b) one homo- and/or copolymer of vinyl acetate,
and at least one release agent chosen from partial glycerides of fatty acids, metal soaps, and inorganic powdered release agents selected from graphite, talc, and mica,
dried the sprayed particle cores, and
in a second stage, spraying the sprayed particle cores with an aqueous dispersion containing at least silicon dioxide,
and drying the sprayed particles cores.

* * * * *